US00PP29169P2

(12) United States Plant Patent
Arisumi et al.

(10) Patent No.: US PP29,169 P2
(45) Date of Patent: Apr. 3, 2018

(54) ***TECOMA* PLANT NAMED 'SUNHORTEDAI'**

(50) Latin Name: *Tecoma hybrida*
Varietal Denomination: Sunhortedai

(71) Applicants: Kenichi Arisumi, Kagoshima (JP); Yasuo Kobayashi, Fukuoka (JP)

(72) Inventors: Kenichi Arisumi, Kagoshima (JP); Yasuo Kobayashi, Fukuoka (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 15/530,290

(22) Filed: Dec. 19, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — C. A. Whealy

(57) ABSTRACT

A new and distinct cultivar of *Tecoma* plant named 'Sunhortedai', characterized by its upright and relatively compact plant habit; vigorous growth habit; freely branching habit; early and freely flowering habit; flowering under high temperature conditions; greyed orange-colored flowers; and low temperature tolerant.

1 Drawing Sheet

Botanical designation: *Tecoma hybrida.*
Cultivar denomination: 'SUNHORTEDAI'.

BACKGROUND OF THE INVENTION

The present invention relates to a new and distinct cultivar of *Tecoma* plant, botanically known as *Tecoma hybrida* and hereinafter referred to by the name 'Sunhortedai'.

The new *Tecoma* plant is a product of a planned breeding program conducted by the Inventors in Chikushino-shi, Fukuoka, Japan. The objective of the breeding program is to create new compact and upright *Tecoma* plants with freely branching habit and attractive flower colors.

The new *Tecoma* plant originated from a cross-pollination in Chikushino-shi, Fukuoka, Japan in September, 2013 of a proprietary selection of *Tecoma hybrida* identified as code name TSTG#2, not patented, as the female, or seed parent with a proprietary selection of *Tecoma hybrida* identified as code name TSAG#1, not patented, as the male, or pollen, parent. The new *Tecoma* plant was discovered and selected by the Inventors as a single flowering plant from within the progeny of the stated cross-pollination in a controlled greenhouse environment in Chikushino-shi, Fukuoka, Japan in June, 2014.

Asexual reproduction of the new *Tecoma* plant by terminal vegetative cuttings in Chikushino-shi, Fukuoka, Japan since June, 2014 has shown that the unique features of this new *Tecoma* plant are stable and reproduced true to type in successive generations.

SUMMARY OF THE INVENTION

Plants of the new *Tecoma* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunhortedai'. These characteristics in combination distinguish 'Sunhortedai' as a new and distinct *Tecoma* plant:

1. Upright and relatively compact plant habit.
2. Vigorous growth habit.
3. Freely branching habit.
4. Early and freely flowering habit.
5. Flowering under high temperature conditions.
6. Greyed orange-colored flowers.
7. Low temperature tolerant.

Plants of the new *Tecoma* can be compared to plants of the female parent selection. Plants of the new *Tecoma* differ primarily from plants of the female parent selection in the following characteristics:

1. Plants of the new *Tecoma* are shorter than plants of the female parent selection.
2. Plants of the new *Tecoma* have smaller flowers than plants of the female parent selection.

Plants of the new *Tecoma* can be compared to plants of the male parent selection. Plants of the new *Tecoma* differ primarily from plants of the male parent selection in the following characteristics:

1. Plants of the new *Tecoma* have longer lateral branches than plants of the male parent selection.
2. Plants of the new *Tecoma* and the male parent selection differ in flower color as plants of the male parent selection have yellow-colored flowers.

Plants of the new *Tecoma* can be compared to plants of *Tecoma hybrida* 'Sunhorteaka', disclosed in U.S. Plant Pat. No. 27,372. Plants of the new *Tecoma* differ primarily from plants of 'Sunhorteaka' in the following characteristics:

1. Plants of the new *Tecoma* are more upright than plants of 'Sunhorteaka'.
2. Leaves of plants of the new *Tecoma* have more leaflets than leaves of plants of 'Sunhorteaka'.
3. Plants of the new *Tecoma* are more freely flowering than plants of 'Sunhorteaka'.
4. Plants of the new *Tecoma* have longer flowers than plants of 'Sunhorteaka'.

5. Plants of the new *Tecoma* and 'Sunhorteaka' differ in flower color as plants of 'Sunhorteaka' have orange red, vivid orange and vivid reddish yellow-colored flowers.

BRIEF DESCRIPTION OF THE PHOTOGRAPHS

The accompanying colored photographs illustrate the overall appearance of the new *Tecoma* plant showing the colors as true as it is reasonably possible to obtain in colored reproductions of this type. Colors in the photographs may differ slightly from the color values cited in the detailed botanical description which accurately describe the actual colors of the new *Tecoma* plant.

The photograph at the top of the sheet comprises a side perspective view of a typical flowering plant of 'Sunhortedai' grown in a container.

The photograph at the bottom of the sheet is a close-up view of a typical inflorescence of 'Sunhortedai'.

DETAILED BOTANICAL DESCRIPTION

The aforementioned photographs and following observations, measurements and values describe plants grown during the summer in 30-cm containers in an outdoor nursery in Higashiomi, Shiga, Japan and under cultural practices typical of commercial *Tecoma* production. During the production of the plants, day temperatures averaged 28° C. and night temperatures averaged 23° C. Plants were ten months old when the photographs and detailed description were taken. In the following description, color references are made to The Royal Horticultural Society Colour Chart, 2007 Edition, except where general terms of ordinary dictionary significance are used.

Botanical classification: *Tecoma hybrida* 'Sunhortedai'.

Parentage:

*Female, or seed, parent*.—Proprietary selection of *Tecoma hybrida* identified as code name TSTG#2, not patented.

*Male, or pollen, parent*.—Proprietary selection of *Tecoma hybrida* identified as code name TSAG#1, not patented.

Propagation:

*Type*.—By terminal vegetative cuttings.

*Time to initiate roots, summer*.—About 15 days at temperatures about 20° C. to 30° C.

*Time to initiate roots, winter*.—About 20 days at temperatures about 23° C. to 28° C.

*Time to produce a rooted young plant, summer*.—After root initiation, about 25 days at temperatures about 20° C. to 30° C.

*Time to produce a rooted young plant, winter*.—After root initiation, about 30 days at temperatures about 23° C. to 28° C.

*Root description*.—Fibrous; typically white in color, actual color of the roots is dependent on substrate composition, water quality, fertilizer type and formulation, substrate temperature and physiological age of roots.

*Rooting habit*.—Freely branching.

Plant description:

*Plant and growth habit*.—Upright and relatively compact plant habit; vigorous growth habit; freely branching habit.

*Plant height*.—About 113 cm.

*Plant width* (*or plant spread*).—About 78 cm.

*Lateral branch description*.—Length: About 49 cm. Diameter: About 5.4 mm. Internode length: About 5.4 cm. Strength: Strong. Texture: Smooth, glabrous. Color: Close to 144A, becoming closer to 146A with development.

Leaf description:

*Arrangement*.—Opposite; pinnately compound with five or seven leaflets per leaf.

*Leaf length*.—About 14.5 cm.

*Leaf width*.—About 13.5 cm.

*Leaflet length*.—About 7.6 cm.

*Leaflet width*.—About 2.9 cm.

*Leaflet shape*.—Elliptic.

*Leaflet apex*.—Acuminate.

*Leaflet base*.—Attenuate.

*Leaflet margin*.—Serrate.

*Leaflet texture, upper and lower surfaces*.—Smooth, glabrous.

*Leaflet venation pattern*.—Pinnate, reticulate.

*Leaflet color*.—Developing leaflets, upper surface: Close to 144A. Developing leaflets, lower surface: Close to 146C. Fully expanded leaflets, upper surface: Close to 137B; venation, close to 145B. Fully expanded leaflets, lower surface: Close to 147C; venation, close to 145C.

*Leaf petioles*.—Length: About 4.1 mm. Diameter: About 1.7 mm. Texture, upper and lower surfaces: Pubescent. Color, upper surface: Close to 144A. Color, lower surface: Close to 145A.

*Leaflet petioles*.—Length: About 1.3 cm. Diameter: About 2.3 mm. Texture, upper and lower surfaces: Smooth, glabrous. Color, upper surface: Close to 144A. Color, lower surface: Close to 145A.

Flower description:

*Flower type and habit*.—Single salverform flowers arranged in terminal panicles; flowers face upright to outwardly; freely flowering habit with about 35 flowers per inflorescence and about 16 inflorescences developing per plant.

*Natural flowering season*.—Early flowering habit, plants begin flowering about six to nine weeks after planting; plants flower in the garden from late spring until autumn in Japan.

*Flower longevity*.—Flowers last about two to three days on the plant; flowers not persistent.

*Fragrance*.—None detected.

*Inflorescence height*.—About 16.4 cm.

*Inflorescence diameter*.—About 14.2 cm.

*Flower buds*.—Height: About 3.7 cm. Diameter: About 1.1 cm. Shape: Club-shaped. Color: Towards the apex, close to 34B; towards the base, close to 26A and 20A.

*Flowers*.—Appearance: Salverform; flared trumpet, corolla fused and five-parted. Diameter: About 3 cm. Height: About 2.9 cm. Throat diameter: About 9.3 mm. Tube length: About 2.7 cm. Tube diameter: About 6.6 mm.

*Corolla*.—Quantity and arrangement: Five petals arranged in a single whorl and fused towards the base into an elongated tube; two upper lobes and three lower lobes. Petal lobe length: About 1 cm. Petal lobe width: About 1.3 cm. Petal lobe shape: Orbicular. Petal lobe apex, upper lobes: Rounded to emarginate. Petal lobe apex, lower lobes: Rounded to truncate. Petal lobe margin: Entire; slightly undulate.

Petal lobe texture, upper and lower surfaces: Smooth, glabrous; velvety. Throat texture: Smooth, glabous. Tube texture: Smooth, glabrous. Color: Upper petal lobes, when opening, upper and lower surfaces: Close to N163B. Lower petal lobes, when opening, upper and lower surfaces: Close to N163A. Upper petal lobes, fully opened, upper surface: Close to N163A to N163B; towards the throat, close to N163C; longitudinal stripes, close to N163A; with development, color becoming closer to 26A and 7A. Lower petal lobes, fully opened, upper surface: Close to N163C; stripes, close to N163A; with development, color becoming closer to 7A. Upper petal lobes, fully opened, lower surface: Close to 169B to 169C. Lower petal lobes, fully opened, lower surface: Close to N163B. Throat: Close to N163B and 13A; stripes, close to N163A. Tube: Close to 26A and 20A.

*Calyx*.—Quantity and arrangement: Five sepals arranged in a single whorl, fused at the base. Sepal length: About 1.6 mm. Sepal width: About 0.9 mm. Sepal shape: Triangular. Sepal apex: Acute. Sepal margin: Entire. Sepal texture, upper and lower surfaces: Smooth, glabrous. Sepal color: When developing and fully opened, upper surface: Close to N144C. When developing and fully opened, lower surface: Close to N144C; towards the base, close to 166A.

*Peduncles*.—Length: About 3.1 cm. Diameter: About 2 mm. Texture: Pubescent. Aspect: Mostly upright. Color: Close to 144A.

*Pedicels*.—Length: About 2.3 mm. Diameter: About 0.7 mm. Texture: Smooth, glabrous. Aspect: Upright to outwardly. Color: Close to 144C.

*Reproductive organs*.—Stamens: Quantity per flower: Typically four. Filament length: About 2.6 cm to 3 cm. Filament color: Close to 4D. Anther size: About 3.7 mm by 4.2 mm. Anther shape: Variable. Anther color: Close to 8C. Pollen amount: Very scarce. Pistils: Quantity: Typically one. Pistil length: About 2.5 cm. Style color: Close to 154D. Stigma shape: Bi-parted. Stigma color: Close to 151D. Ovary color: Close to 144D.

*Seeds and fruits*.—Seed and fruit production have not been observed on plants of the new *Tecoma*.

Disease & pest resistance: Plants of the new *Tecoma* have not been noted to be resistant to pathogens and pests common to *Tecoma* plants.

Garden performance: Plants of the new *Tecoma* have been observed to tolerate wind, rain and temperatures ranging from about −5° C. to about 35° C.

It is claimed:

1. A new and distinct *Tecoma* plant named 'Sunhortedai' as illustrated and described.

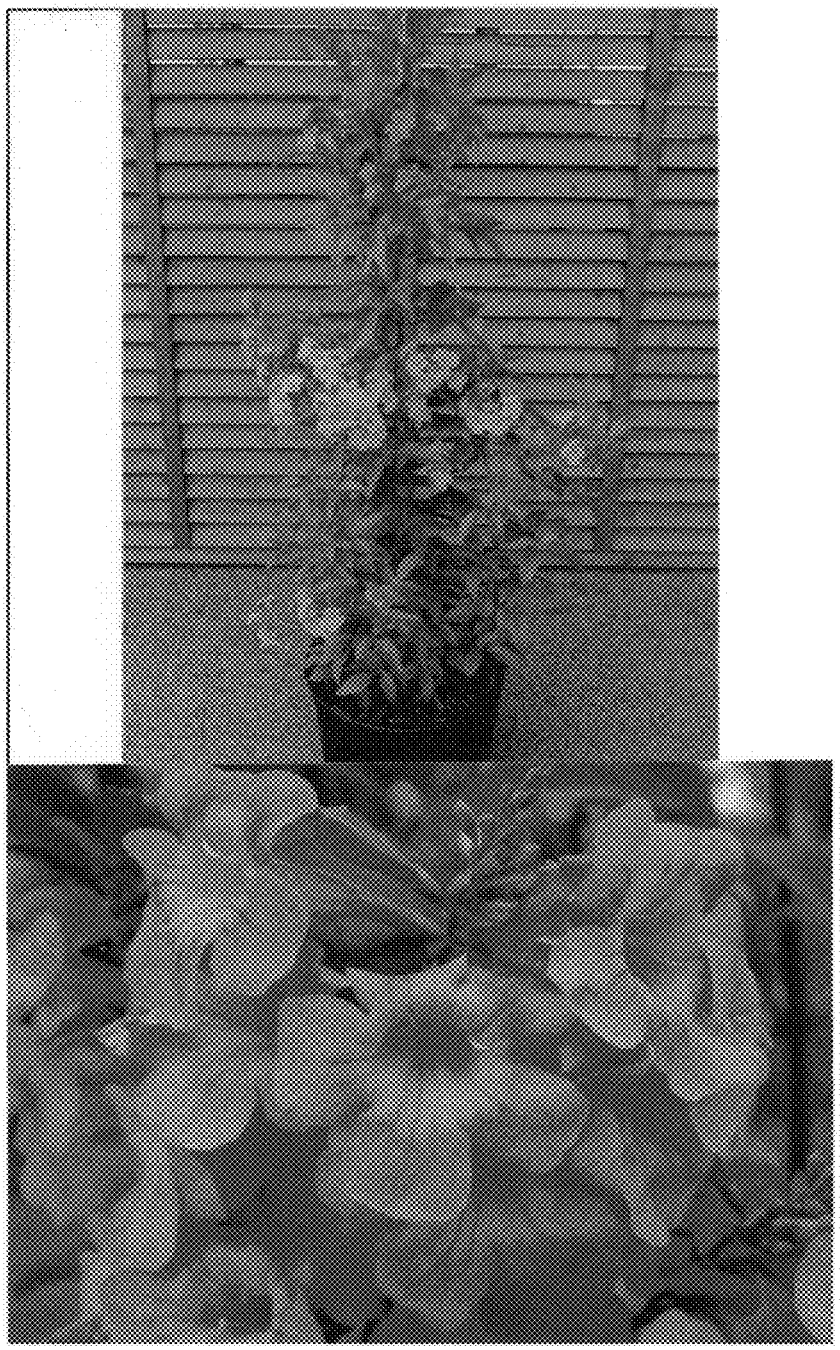

* * * * *